United States Patent [19]

Sano et al.

[11] Patent Number: 5,093,531
[45] Date of Patent: Mar. 3, 1992

[54] POLYETHYLENE GLYCOL SUBSTITUTED PHENYL GLYOXALS

[75] Inventors: Akihiko Sano; Hiroo Maeda, both of Osaka; Yoshiyuki Kai, Hyogo; Keiichi Ono, Osaka, all of Japan

[73] Assignee: Sumitomo Pharmaceuticals Company, Limited, Osaka, Japan

[21] Appl. No.: 347,902

[22] Filed: May 5, 1989

[30] Foreign Application Priority Data

May 6, 1988 [JP] Japan ................. 63-110931

[51] Int. Cl.$^5$ ............................................. C07C 49/76
[52] U.S. Cl. .................................. 568/337; 530/402; 530/406
[58] Field of Search ................. 530/402, 406; 568/308, 568/335, 337; 526/313, 316

[56] References Cited

U.S. PATENT DOCUMENTS 4,179,337 12/1979 Davis et al. .................... 435/181

FOREIGN PATENT DOCUMENTS 154316 9/1985 European Pat. Off. .

OTHER PUBLICATIONS

Takahashi et al., "Journal of Biological Chemistry", 243(10) 6171-6179 (1968).
"Patent Abstracts of Japan", vol. 010, No. 390, (C-394) (2447) Dec. 26, 1986, Abstract of JP-A-178926.
Abuchowski et al., "Cancer Biochemistry Biophysics", 7 175-186 (1984).
Biochemical Experiment Method 12, Chemical Modification of Protein (first vol.) 61-69 Gakkai Publication Center (1981).
Yashimoto et al., "Japan Journal of Cancer Res. (Gann)", 77, 1264-1270 (1986).
Leonard et al., "Tetrahedron", 40, 1581-1584 (1984).
Beauchamp et al., "Analytical Biochemistry", 131, 25-33 (1983).
Crossland et al., "J. Org. Chem.", 35, 3195-3196 (1970).
Sekera et al., "J. Amer. Chem. Soc.", 55, 345-349 (1933).
Cason et al., "J. Org. Chem.", 26, 3645-3649 (1961).
Hooz et al., "Canadian Journal of Chemistry", 46, 86-87 (1968).
Riordan, "Biochemistry", 12, 3915-3623 (1973).
Patthy et al., "Journal of Biological Chemistry", 250, 557-564 (1975).

*Primary Examiner*—F. T. Moezie
*Assistant Examiner*—Andrew G. Rozycki
*Attorney, Agent, or Firm*—Wenderoth, Lind & Ponack

[57] ABSTRACT

A polyethylene glycol derivative of the formula

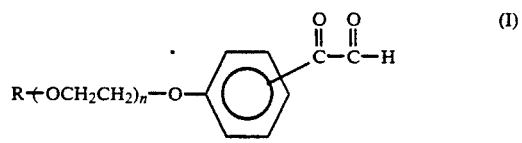

wherein R represents a lower alkyl and n represents an optional positive integer which renders the average molecular weight of the polyethylene glycol moiety about 1,000 to 12,000, a peptide modified by said polyethylene glycol derivative and a method for production thereof.

The polyethylene glycol derivative (I) is capable of modifying the guanidino groups in peptides. The peptides modified by the polyethylene glycol derivative (I) are extremely stable, are considerably delayed in biological clearance (i.e. the durability is extended) and exhibit their physiological activities effectively over the long period.

2 Claims, No Drawings

POLYETHYLENE GLYCOL SUBSTITUTED PHENYL GLYOXALS

BACKGROUND OF THE INVENTION

This invention relates to polyethylene glycol derivatives which are novel and of the use as peptide (particularly protein)-modifying reagents, peptides having guanidino group which are modified by said polyethylene glycol derivatives and the methods for producing them In recent years, with the development of to research in proteins, a great number of peptides, in particular, physiologically active proteins having various actions have been found. Owing to the progress of genetic recombination techniques and organic synthetic methods of peptides, it has become possible to obtain these physiologically active peptides and their structurally analogous compounds in a large amount. Many of these peptides having special activity are extremely useful as pharmaceuticals.

However, it is known that the clearance of peptides which has been administered in the circulatory system is generally very fast, and therefore the improvement in durability of such peptides has been desired. Besides, since there is a risk of causing serious symptoms due to the production of antibodies in the case where the peptides are obtained from different species of animals or designed by peptide-protein engineering, and they are different from those from humans in structure, the improvement of the antigenicity of said proteins is desired.

In order to use these peptides as pharmaceuticals, it is necessary to solve said problems in the aspect of their antigenicity and durability. The method of modifying the peptides chemically with macromolecular compounds is known to be extremely effective as the means by which to solve the above-mentioned problems.

Thus, polyethylene glycol derivatives have been widely used as peptide-modifying macromolecular reagents because they have excellent characteristics that they do not have immunogenicity themselves and that they do not affect the three-dimensional structures of peptides (proteins) in aqueous solutions.

In modifying peptides with polyethylene glycol derivatives, there have been known, as the general methods for activation, the activation method with triazine derivatives [Inada et al, Jpn. J. Cancer Res. (Gann), 77, 1264–1270 (1986)], the active ester method with N-hydroxysuccinimide [Leonardo M. et al, Tetrahedron, 40, 1581–1584 (1984)], the activation method with carbonyldiimidazole [Charles. 0. Beecham et al, Anal. Biochem, 131, 25–33 (1983)], the activation method with aldehydes [Fujino et al, Japanese Patent Application Unexamined Publication (Kokai) No. 178926/1986] and so on.

Any of these modification methods, however, comprise modifying the amino groups at the N-terminal or in the side chain of the lysine residues of the peptides.

On the other hand, in many peptides, the amino groups at the N-terminal or those in the side chain of the lysine play an important role for the expression of physiological activities. Therefore, in the case of these peptides, modifying the amino groups with the above-mentioned activating reagents is not preferable because such modification results in the reduction of activities. Besides, in the case of the method in which the lysine residues alone are modified, there is a limitation on the sites of modification. As it is considered to be effective for the puropose of controlling properties of peptides to modify various sites other than the amino groups, extremely significant is the development of reagents modifying the other functional groups.

As the reagents modifying the other functional groups hitherto known, mention is made of maleimide derivatives modifying the mercapto group and amino derivatives modifying the carboxyl group [Frank F. Davis et al, Japanese Patent Application Examined Publication (Kokoku) No. 23587/1981] and so on.

However while, unless mercapto groups exist in the form of mercapto groups on the surface of the molecules, the modification thereof is considered to be difficult, and there are a very few peptides having such structures.

In addition, in the case of modification with amino derivatives, it is difficult to react the desired modifying reagent alone selectively since the side reactions by the amino groups in the peptides occur.

On the other hand, as the lower molecular reagents for modifying guanidino groups in peptides, there are known phenylglyoxal (Journal of Biological Chemistry, vol. 248, 6171 (1968)), 2,3-butanedione (Biochemistry, vol. 12, 3915 (1973)), 1,2-cyclohexanedione (Journal of Biological Chemistry, vol. 250, 557 (1975)) and so on. However, there have not been so far known any polyethylene glycol derivatives capable of modifying guanidino groups in peptides.

SUMMARY OF THE INVENTION

One of the objects of the present invention is to provide polyethylene glycol derivatives which are capable of modifying guanidino groups in peptides selectively.

Another object of this invention is to provide modified peptides which can be obtained by using said polyethylene glycol derivatives.

Furthermore, still another object is to provide methods for the production of said modified peptides The present inventors conducted extensive research and studies for the purpose of attaining the above-mentioned objects to find that the below-mentioned polyethylene glycol derivatives (I) could selectively modify guanidino groups in peptides. Further research and studies resulted in the completion of the present invention.

The first embodiment of the present application relates to polyethylene glycol derivatives of the formula

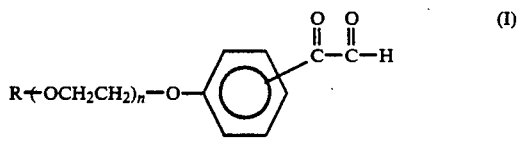

wherein R represents a lower alkyl and n represents an optional positive integer which renders the average molecular weight of the polyethylene glycol moiety about 1,000–12,000.

The second embodiment of the present application relates to modified peptides which can be obtained by reacting the polyethylene glycol derivatives (I) with peptides having guanidino group(s).

The third embodiment of the present invention relates to the methods for producing modified peptides which comprise reacting polyethylene glycol derivatives (I) with peptides having guanidino group(s).

DETAILED DESCRIPTION OF THE INVENTION

In the present specification, the lower alkyl groups represented by R may be in a straight-chain or branched chain form. Preferred are, for example, lower alkyl groups having 1 to 4 carbon atoms such as methyl, ethyl, n-propyl, isopropyl, n-butyl and the like.

The polyethylene glycol derivatives (I) of the present invention can be easily produced by the following methods:

That is, by reacting a monoalkoxypolyethylene glycol (II) of the formula

R(OCH₂CH₂)ₙ—OH     (II)

wherein R and n are of the same meanings as defined above with an appropriate activating reagent, preferably in the presence of a base, there is obtained activated compound (III) of the formula

R(OCH₂CH₂)ₙ—X'     (III)

wherein X' represents an alkylsulfonyloxy (e.g. a lower alkylsulfonyloxy having 1–4 carbon atoms such as methylsulfonyloxy, ethylsulfonyloxy or the like), an aromatic sulfonyloxy (e.g. toluenesulfonyloxy) or a halogen (chlorine, bromine etc.).

As the activating reagents to be used in the reaction, mention may be made of, for example, ① alkylsulfonyl chlorides (As the alkyl moiety, preferred are the same lower alkyls as the above-mentioned alkyls. There may be mentioned, for example, methylsulfonyl chloride, ethylsulfonyl chloride and the like.) [Ronald K. Crossland et al, J. Org. Chem. 35, 95 (1970)], ② aromatic sulfonyl chlorides (e.g. toluenesulfonyl chloride etc.) [Vladimir C. Sekera et al, J. Amer. Chem. Soc. 55, 345 (1933)], ③ phosphorus pentabromide [James Cason et al, J. Org. Chem. 26, 3645 (1961)] and the like, and further, ④ the compounds of the formula C(X)hd 4 [wherein X represents a halogen (e.g. chlorine, bromine)] which are used in the presence of a compound of the formula (R')₃P [wherein R' represents an alkyl group (e.g. octyl), an aryl group (e.g. phenyl) or a dialkylamino group (e.g. dimethylamino)] [J. Hooz et al, Can. J. Chem. 46, 86 (1968)], and the like.

As the bases to be used in the reaction, mention may be made of pyridine, tertiary organic bases such as trialkylamine (e.g. triethylamine) and inorganic bases such as sodium hydroxide, potassium hydroxide, sodium carbonate, sodium hydride. As the reaction solvent, there can be used any per se inert solvents such as N,N-dimethylformamide, benzene, toluene, lower dialkyl ether, carbon tetrachloride, chloroform, methylene chloride, dioxane, tetrahydrofuran and the like. Some of the above-mentioned bases such as pyridine can be used as solvents themselves. The reaction temperature is usually in the range of from 0° C. to 150° C.

Thereafter, by reacting the activated compound (III) with hydroxyacetophenone in an appropriate solvent such as N,N-dimethylformamide or tetrahydrofuran in the presence of an appropriate base exemplified by an inorganic base such as potassium carbonate or sodium carbonate or an organic base such as triethylamine, tri-n-butylamine or diazabicyclo2,2,2-undecene under heating at a temperature ranging from 60° C. to 120° C., an acetophenone derivative (IV) of the formula

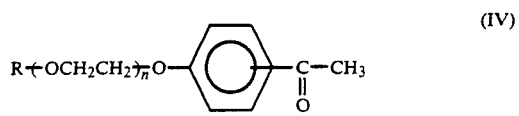

wherein R and n are of the same meanings as mentioned above can be obtained.

By oxidizing the obtained acetophenone derivative (IV) with the use of a suitable oxidizing agent such as selenium dioxide in a solvent such as N,N-dimethylformamide, or dioxane inert to the reaction at a temperature ranging from 60° C. to 120° C., the objective polyethylene glycol derivative (I) can be produced.

The thus-produced polyethylene glycol derivatives (I) can be separated and purified to obtain ones having an optional purity by a per se known means.

Throughout the present specification, peptides mean compounds wherein two or more amino acids are bonded to each other by a peptide linkage. Preferable are proteins and substances having structures similar to the structures of proteins.

At least one of the constituent amino acids has at least one guadino group (e.g. arginine).

As such peptides, in particular proteins, mention may be made of, for example, peptides having physiological activities such as substance P (hypothalamic hormone), corticotropin, lipotropin, melanotropin (pituitary hormone), arginine-vasopressin (neurohypophysical hormone), parathyroid hormone (thyroid hormone), thymopoietin (thymic factor), insulin, glucagon (pancreatic hormone), nerve growth factor, epidermal growth factor, insulin-like growth factor-I, human transformation growth factor, growth hormone-releasing factor, i.e. GRF, basic fibroblast growth factor (growth factor), secretin, cholecystokinin, vaso active intestinal peptide, motilin (gastrointestinal hormone), gonadotropin (chorion hormone), gonadotropic hormone-releasing hormone (gonadotropic hormone), relaxin (ovarian hormone), blood coagulation factor VIII factor and IX factor (hemophilia factor), streptokinase, fibrinolysin, deoxyribonuclease, superoxide dismutase, elastase, asparaginase (enzyme), tissue plasminogen-activator, i.e. tPA, urokinase (fibrinolysis factor), lymphokine [e.g. interleukin I and II], granulocyte macrophage.colony-stimulating factor, i.e. GM-CSF (stimulating factor), erythropoietin (erythropoietic stimulating factor), calcitonin gene related peptide (Ca-regulating hormone), atrial natriuretic peptide (diuretic hormone) and so on, and substances having structures similar to these of said peptides, which have the same physiological activities as those of said peptides.

In the above-mentioned exemplification, the uses of the peptides are described in the parentheses.

In the present invention, the peptides include any peptides that are produced by genetic engineering methods, that are from various animals including human beings and that are produced by synthesis.

The production of the modified peptides of the present invention can be carried out by reacting polyethylene glycol derivatives (I) with peptides having guanidino group(s).

In the reaction, the polyethylene glycol derivative (I) is used preferably in about equimolar to 100 times molar amount relative to the guanidino group in the peptide. However, when it is desired to obtain peptides modified to a lower degree, the polyethylene glycol derivative (I) can be used in an amount not more than about 1 mol (e.g. 0.1 to 1 time mol) on the same basis. By adjusting the molar ratio of the polyethylene glycol derivative (I) relative to the quadino group of the peptide having guadino group, the reaction temperature, pH and the like, the degree of modification can be optionally selected. As the solvent to be used in the reaction, there can be used any solvent which does not prevent the reaction. Such solvents include, for example, buffer solutions such as tris hydrochloric acid buffer solution, an aqueous solution of sodium carbonate, an aqueous solution of sodium hydrogen carbonate, N-ethylmorpholineacetic acid buffer solution, sodium maleate buffer solution and sodium acetate buffer solution. There can be added an organic solvent which does not inactivate the peptides and are inert to the reaction, exemplified by lower alcohols such as methanol, ethanol and propanol, acetonitrile, dioxane, tetrahydrofuran and the like. The pH of the reaction can be generally selected in the range of from 6 to 10. The pH in the neutral range to weak basic range is particularly preferable. However, in the case of peptides having unprotected α-amino group at the amino-terminal, preferred is pH 5.5 to 6.5 which is acidic. The reaction temperature may be any temperature at which the peptides are not inactivated, and is preferably in the range from 0° C. to 25° C. The reaction can be usually conducted in the dark. The sufficient reaction time is in the range from 3 to 72 hours.

After the completion of the reaction, the reaction mixture is purified by a conventional protein-purification method such as salting-out, gel filtration, ion exchange chromatography, adsorption chromatography, affinity chromatography, ultrafiltration and preparative reversed phase HPLC, to obtain the objective modified peptides.

It is known from research regarding phenylglyoxal as a lower molecular modifying reagent, under such severe conditions where the concentration of the reagent is enhanced, the side reaction of the elimination of the α-amino group at the amino-terminal occurs. (Biochemical Experiment Method 12, Chemical Modification of Protein (the first volume) pp 62 - 69 (Gakkai Publication Center, 1981), Journal of Biological Chemistry vol. 248, 6171 (1968)). In the modification with the use of polyethylene glycol derivatives (I) of the present invention, the possibility of the same side reaction is presumable. In the case where there is a fear of such a side reaction, sometimes advantageous are the methods which comprise protecting the amino groups in peptides having guanidino group with an appropriate protective group and then reacting the protected peptides with the polyethylene glycol derivatives (I), followed by deprotection of the amino-protective groups to produce the modified peptides. As the amino-protective groups, usable are any protective groups that are not reactive with the polyethylene glycol derivatives (I), and can be eliminated without inactivating the peptides. Such protective groups are exemplified by succinyl group, maleyl group, 2-methylmaleyl group, 2,3-dimethylmaleyl group, exo-cis-3,6-endooxo-$\Delta^4$-tetrahydro phthaloyl group, exo-cis-3,6-endoxyhexahydro phthaloyl group, tetrafluorosuccinyl group and the like. Introduction of the protective groups can be conducted by the known methods in the art. As the protective group-introducing reagents, usable are the corresponding acid anhydrides, acid halogenides, active esters and the like. In general, the corresponding acid anhydrides are often used. As the reaction solvents, usable are any solvents that do not prevent the reaction Examples of such solvents include an aqueous solution of sodium carbonate, an aqueous solution of sodium hydrogen carbonate, N-ethylmorpholine-acetic acid buffer solution, sodium acetate buffer solution, phosphoric acid buffer solution and the like. There can be added an organic solvent which does not inactivate the peptide and is inert to the reaction. Such organic solvents are exemplified by lower alcohols such as methanol, ethanol and propanol, acetonitrile, dioxane, tetrahydrofuran and the like. The pH of the reaction can be preferably selected in the range from 6 to 10. The pH in the neutral range to weak basic range is particularly preferable. The reaction temperature may be any temperature at which the peptide is not inactivated, and is preferably in the range from −5° C. to 25° C. The sufficient reaction time is from 30 minutes to 36 hours.

After the completion of the reaction, the reaction mixture is purified by a conventional peptide and protein-purification method such as salting-out, gel filtration, ion exchange chromatography, adsorption chromatography, affinity chromatography, ultrafiltration, preparative reversed phase HPLC and the like to give the objective amino-protected peptides. The reaction mixture can, without being purified, be directly reacted with the polyethylene glycol derivative (I) to give the amino group-protected peptide modified by the polyethylene glycol derivative.

The reaction of an amino group-protected peptide having guanidino group with a polyethylene glycol derivative (I) and the purification after the completion of the reaction can be conducted under the same reaction conditions and by the same purification method as the above-mentioned reaction conditions and purification method.

The deprotection of the amino-protective groups can be conducted by maintaining the reaction mixture in an acidic condition. The pH is preferably selected in the range from 1 to 6. As the methods for maintaining acidic conditions, any methods can be used unless they fail to inactivate the peptide. Such methods include, for example, the methods with the use of acids (organic acids such as acetic acid trifluoroacetic acid and organic sulfonic acid; inorganic acids such as hydrochloric acid and the like) the methods with the use of acidic resins such as Dowex 50W, the methods with the use of buffer solutions such as phosphoric acid buffer solution, citric acid buffer solution, sodium acetate buffer solution and so on, and the methods comprising the above-mentioned methods in combination. The reaction is generally conducted in an aqueous solution alone. In some cases, it is preferable to add an organic solvent which does not inactivate the peptide and is inert to the reaction. Such organic solvents are exemplified by lower alcohols such as methanol, ethanol, and propanol, acetonitrile, dioxane, tetrahydrofuran and the like. As the reaction temperature, permissible is any temperature at which the peptide is not in activated. The reaction temperature is preferably in the range from 0° C. to 40° C. A sufficient reaction time ranges from 5 minutes to 60 hours.

After the completion of the reaction, the reaction mixture is purified by a conventional method for protein-purification such as salting-out, gel filtration, ion exchange chromatography, adsorption chromatography, affinity chromatography, ultrafiltration, preparative reversed phase HPLC and the like to afford the objective modified peptide.

The modified peptides of the present invention can be formulated into conventional pharmaceutical preparations in a suitable conventional form such as injectable solutions for subcutaneous, intramuscular or intravenous administration. These pharmaceutical preparations can be produced by the per se known methods.

The modified peptides formulated in the form of such pharmaceutical compositions can be administered to mammals (human beings, monkeys, cows, horses, dogs, pigs etc.).

For example, in the case where the chemically modified tPA as obtained in accordance with Example 3 is administered for the treatment myocardial infarction, the daily dose is usually 1 - 100 mg, which is administered in one dose to several times divided doses.

The polyethylene glycol derivatives (I) of the present invention are capable of selectively modifying the guanidino groups in peptides.

The peptides modified by the polyethylene glycol derivatives (I), as compared with the corresponding nonmodified peptides, are extremely stable, are considerably delayed in biological clearance (i.e. the durability is extended) and exhibit their physiological activities effectively over the long period.

Besides, the modified peptides retain the physiological activities which the non-modified peptides possess as is. Thus, the modified peptides are very effective as the pharmaceuticals.

The present invention is in further detail explained by the following examples, which are not limitative to the present invention.

In the following description, each abbreviation means the following respectively.

Asx.: aspartic acid or asparagine
Glx.: glutamic acid or glutamine
Ser.: serine,
His.: histidine,
Thr.: threonine,
Pro.: proline,
Val.: valine,
Ile.: isoleusine,
Phe.: phenylalanine,
Gly.: glycine
Arg.: arginine
Ala.: alanine
Tyr.: tyrosine
Met.: methionine
Leu.: leusine
Lys.: lysine

EXAMPLE 1

(1) Production of monomethoxypolyethylene glycol tosylate

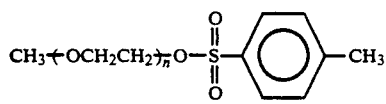

Polyethylene glycol monomethyl ether (average molecular weight 5000, 40 g) was dissolved in a mixed solvent of 160 ml of toluene and 80 ml of methylene chloride. p-Toluenesulfonyl chloride (8.0 g) was added thereto, followed by addition of 5.8 ml of triethylamine. The mixture was stirred at room temperature for 6 hours. Thereafter, p-toluenesulfonyl chloride (8.0 g) was further added, and the mixture was stirred for 10 hours. The insoluble matter was filtered off. The filtrate was concentrated under reduced pressure. The obtained residue was purified by silica gel column to give 32.4 g of the title monomethoxypolyethylene glycol tosylate (Yield 78.6%), m.p. 55°-57° C.

$^1$H-NMR (CDCl$_3$), TMS, 90 (MHz), δ2.18 (s), δ3.38 (s), δ3.62 (s), δ7.3 (ABq)

(2) Production of 4-monomethoxypolyethylene glycol-acetophenone

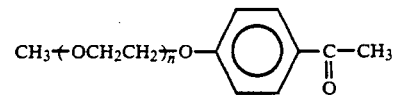

Monomethoxypolyethylene glycol tosylate (20 g) obtained in (1) and 4-hydroxyacetophenone (5.6 g) were dissolved in 200 ml of N,N-dimethylformamide. Potassium carbonate (5.6 g) was added thereto. The mixture was stirred in an oil bath at 120° C. for 4.hours.

The insoluble matter was filtered off. The filtrate was concentrated under reduced pressure. The obtained residue was purified by silica gel column to give the title 4-monomethoxypolyethylene glycol-acetophenone (14.7 g) (Yield 73.9%), m.p. 55°-57° C.

$^1$H-NMR (CDCl$_3$), TMS, 90 (MHz), δ2.42 (s), δ3.32 (s), δ2.64 (s), δ7.64 (ABq)

(3) Production of 4-monomethoxypolyethylene glycol-phenylglyoxal

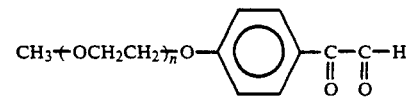

4-monomethoxypolyethylene glycol-acetophenone (50 g) as obtained in (2) was dissolved in 500 ml of 1,4-dioxane. Selenium dioxide (10.8 g) was added thereto, and the mixture was refluxed for 4 hours. The insoluble matter was filtered off. The filtrate was concentrated under reduced pressure. The obtained residue was purified by silica gel chromatography to give 27 g of 4-monomethoxypolyethylene glycol-phenylglyoxal (Yield 53.8%), m.p. 55°-57° C.

$^1$H-NMR (CDCl$_3$), TMS, 90 (MHz), δ3.38 (s), δ3.66 (s), δ7.48 (ABq)

EXAMPLE 2

Production of tissue-plasminogen activator (t-PA) modified by a polyethylene glycol derivative (I)

After 4.6 ml of a 0.2M aqueous solution of sodium hydrogen carbonate (1MKSCN, pH 8.5) was added to 420 μl of a t-PA solution (12 mg/ml, 0.1M sodium chloride, pH 3), 150 mg of 4-monomethoxypolyethylene glycol-phenylglyoxal obtained in Example 1 was added thereto. The mixture was stirred at room temperature for 4 hours. With an aqueous solution of 1N hydrochloric acid, the pH was adjusted to 3.

The reaction mixture was subjected to dialysis in a 0.6% aqueous solution of acetic acid, followed by lyophilization. The obtained lyophilized product was purified by gel filtration with Sephacryls-200 column, followed by purification by Sephadex G-50F to give 1.9 mg of the objective compound. The results of the amino acid analysis of the resultant mixture of 24 hours' treatment for acid decomposition with 6N hydrochloric acid at 110° C. are as follows:

Asx. 49.0 (50); Glx. 51.8 (52); Ser. 46.7 (48);
Gly. 45.4 (43); His. 16.4 (16); Arg. 26.7 (35);
Thr. 24.3 (25); Ala.* 32 (32); Pro. 30.8 (29);
Tyr. 23.7 (24); Val. 21.8 (25); Met. 4.1 (5);
Ile. 17.1 (19); Leu. 40.6 (39); Phe. 16.6 (16);
Lys. 22.8 (21);

* means standard amino acid and the figures in parentheses are theoretical values.

From the above results, it is found that the Arg residues are selectively modified.

The behavior of the objective compound in high performance liquid chromatography was as follows:

Reversed phase high performance liquid chromatography

Column: μ-Bondasphere-C$_4$ (3.9×150 mm) (Manufactured by Waters Corp.)
Eluent: Gradient
  A Solution: Water (0.1% trifluoroacetic acid)
  B Solution: Acetonitrile (0.1% trifluoroacetic acid)
  Initial concentration of B Solution: 30%
  Concentration gradient: 1%/min.
Flow rate: 1 ml/min.
Detection wavelength : 214 nm
Retention time : 15.2 minutes Molecular sieve high performance liquid chromatography Column : TSK G3000SW 7.5×600 mm (Manufactured by TOSOH Corp.)
Eluent: 0.1M aqueous solution of sodium chloride (pH 4.0)
Flow rate: 1 ml/min.
Retention time: 11.4 minutes

EXAMPLE 3

Production of tissue-plasminogen activator (t-PA)II modified by a polyethylene glycol derivative (I)

After 4.6 ml of a 0.2 M aqueous solution of sodium hydrogen carbonate (1M KSCN, pH 8.5) was added to 420 μl of a solution of t-PA (12 mg/ml, 0.1M sodium chloride, pH 3), 25.2 mg of 4-monomethoxypolyethylene glycol-phenylglyoxal obtained in Example 1 was added thereto. The mixture was stirred at room temperature for 3 hours. With a 1N aqueous solution of hydrochloric acid, the pH was adjusted to 4. The reaction mixture was subjected to high performance liquid chromatography with the use of μ-Bondasphere-C$_4$, 5 μ, 300 A, φ3.9×150 mm column for preparative purification. The elution of the objective compound was conducted with the concentration of acetonitrile enhanced from 33% to 43% at the rate of 0.5%/min. with the use of an aqueous solution of acetonitrile with trifluoroacetic acid added at the concentration of 0.1% at the flow rate of 1 ml/min. The elution time of the obtained product in the high performance liquid chromatography on the above-mentioned conditions was 13.2 minutes. Yield 0.8 mg. By this procedure, there could be obtained t-PA modified to a lower degree by a polyethylene glycol derivative (I).

In SDS gel electrophoresis, the obtained objective compound electrophoresed at the position of about 90000 in terms of protein.

EXAMPLE 4

Production of growth hormone-releasing factor [GRF (1-29) NH$_2$] modified by a polyethylene glycol derivative (I)

In 7.3 ml of water was dissolved 100 mg of growth hormone-releasing factor [GRF (1-29) NH$_2$]. Thereto were added 66 ml of a 0.1M phosphoric acid buffer solution (pH 7.2) and 3.6 g of 4-monomethoxypolyethylene glycol-phenylglyoxal obtained in Example 1. The mixture was stirred at room temperature in the dark overnight. The reaction mixture (20 ml) was subjected to dialysis, followed by lyophilization to give 657 mg of the crude product. This product was purified by gel filtration with the use of Sephacryl S-200 column φ2×70 cm manufactured by Pharmacia Corp. with a 0.1M aqueous solution of sodium chloride at the flow rate of 1 ml/min. The obtained fraction was subjected to high performance liquid chromatography for preparative purification with the use of YMC Pack AM304 ODS φ1×30 cm column manufactured by Yamamura Chemicals. The elution of the objective compound was conducted with the concentration of acetonitrile enhanced from 0% to 80% at the rate of 2%/min. with the use of an aqueous solution of acetonitrile with trifluoroacetic acid added thereto at the concentration of 0.1% at the flow rate of 3 ml/min. Yield 30.0 mg.

The results of the amino acid analysis by 24 hours' treatment for acid decomposition with 6N hydrochloric acid at 110° C. are as follows:

Asx. 2.94 (3); Glx. 207 (2); Ser. 2.81 (3);
Gly. 1.36 (1); Arg. 1.04 (3); Thr. 0.97 (1);
Ala. 1.48 (3); Tyr. 1.02 (2); Val. 0.77 (1);
Met. 0.70 (1); Ile. 2.01 (2); Leu.* 4.00 (4);
Phe. 0.96 (1); Lys. 1.52 (2);

* means standard amino acid and the figures in the parentheses are theoretical values.

The behavior of the objective compound in high performance liquid chromatography is as follows:

Reversed phase high performance liquid chromatography

Column: μ-Bondasphere-C$_{18}$ (3.9×150 mm) (Manufactured by Waters Corp.)
Eluent: Gradient
  A Solution: Water (0.1% trifluoroacetic acid)
  B Solution: Acetonitrile (0.1% trifluoroacetic acid)
  Initial concentration of B Solution: 20%
  Concentration gradient: 1%/min.
Flow rate: 1 ml/min.
Retention time: 26.9 minutes Molecular sieve high performance liquid chromatography Column: Shodex OH-B804 7.6×500 mm (Showa Denko)
Eluent: 0.1M aqueous solution of sodium chloride (pH 4)
Flow rate: 1 ml/min.
Retention time: 13.8 minutes

EXAMPLE 5

Production of granulocyte macrophage colony-stimulating factor (GM-CSF) modified by a polyethylene glycol derivative (I)

To GM-CSF (500 μg/ 500 ml aqueous solution) was added a solution of 11.0 mg of 4-monomethoxypolyethylene glycolphenylglyoxal obtained in Example 1 in 500 μl of 0.1M phosphoric acid buffer solution (pH 8.5). The mixture was stirred at room temperature for 7 hours. The reaction mixture was subjected to high performance liquid chromatography for preparative purification with the use of μ-Bondasphere-$C_{18}$ (5 μ, 100 Å, φ3.9×150 mm) column manufactured by Waters Corp. The elution of the objective compound was conducted with the concentration of acetonitrile being enhanced from 36% to 56% at the rate of 1%/min. with the use of an aqueous solution of acetonitrile with trifluoroacetic acid added at the concentration of 0.1%. Yield 0.4 mg. The elution time of the obtained purified product in the high performance liquid chromatography on the above-mentioned conditions was 12.3 minutes.

EXAMPLE 6

Production of growth hormone-releasing factor [GRF(1-44)$NH_2$] modified by a polyethylene glycol derivative (I):

To 20 mg of growth hormone-releasing factor [GRF(1-44)$NH_2$] in 20 ml of a 0.2M $NaHCO_3$ solution (pH 8.18) was added a solution of 18.5 mg of 4-monomethoxypolyethylene glycol-phenylglyoxal (1/6 equivalent amount relative to guanidino) and the mixture was left standing at room temperature in shading for 5.5 hours. After adjusting the pH of the reaction mixture to 2.4 with an aqueous solution of 1N hydrochloric acid, the mixture was purified by gel filtration with Sephacryl S-200 Superfine column (φ2.6×84 cm) manufactured by Pharmacia Corp., Sweden. The objective fraction was subjected to desalting and concentration by ultrafiltration with the use of YM-10 membrane manufactured by Amicon Corp., USA. The obtained solution containing the objective compound was further subjected to secondary purification by reversed phase high performance liquid chromatography with the use of YMC-ODS, A-211, 5 μ, φ4.6×250 mm column manufactured by Yamamura Chemicals to give the objective compounds A and B.

The results of the amino acid analysis by 24 hours' treatment for acid decomposition of the objective compound A with 6N hydrochloric acid-phenol at 110° C. are as follows:

Asx. 3.83 (4); Glx. 7.18 (7); Ser. 3.82 (4);
Gly. 3.49 (3); Arg. 4.87 (6); Thr. 1.17 (1);
Ala. 5.18 (5); Tyr. 1.89 (2); Val. 1.10 (1); Met. 0.78 (1);
Ile. 1.95 (2); Leu.* 5.00 (5); Phe. 0.99 (1); Lys. 2.26 (2)
* means standard amino acid and the figures in parentheses are theoretical values.

The behavior of the objective compound A in high performance liquid chromatography is as follows:

Reversed phase high performance liquid chromatography

Column: YMC-ODS, A-211, 5 μ, φ4.6×250 mm (Manufactured by Yamamura Chemicals)
Eluent: Gradient
 A Solution: Water (0.1% trifluoroacetic acid)
 B Solution: Acetonitrile (0.1% trifluoroacetic acid)
 Initial concentration of B Solution: 25%
 Concentration gradient: 1%/min.
Flow rate: 1 ml/min.
Detection wavelength: 214 nm
Retention time: 20.2 minutes The results of the amino acid analysis by 24 hours' treatment for acid decomposition of the objective compound B with 6N hydrochloric acid-phenol at 110° C. are as follows:

Asx. 3.82 (4); Glx. 6.89 (7); Ser. 3.70 (4);
Gly. 3.17 (3); Arg. 4.17 (6); Thr. 1.12 (1);
Ala. 5.31 (5); Tyr. 1.80 (2); Val. 1.05 (1);
Met. 0.91 (1); Ile. 2.05 (2); Leu.* 5.00 (5);
Phe. 0.98 (1); Lys. 2.31 (2)
* means standard amino acid and the figures in the parentheses are theoretical values.

The behavior of the objective compound B in high performance liquid chromatography is as follows:

Reversed phase high performance liquid chromatography

Column: YMC-ODS, A-211, 5 μ, 4.6×250 mm (Manufactured by Yamamura Chemicals)
Eluent: Gradient
 A Solution: Water (0.1% trifluoroacetic acid)
 B Solution: Acetonitrile (0.1% trifluoroacetic acid)
 Initial concentration of B Solution 25%
 Concentration gradient 1%/min.
Flow rate: 1 ml/min.
Detection wavelength: 214 nm
Retention time: 21.8 minutes

EXAMPLE 7

Production of growth hormone-releasing factor [GRF(1-29)$NH_2$]II modified by a polyethylene glycol derivative (I)

To 30 mg of growth hormone-releasing factor [GRF(1-29)$NH_2$] in 3 ml of a 0.02M phosphoric acid buffer solution (pH 5.52) was added a solution of 128.5 mg of 4-monomethoxypolyethylene glycol-phenylglyoxal (1 equivalent amount relative to guanidino) and the mixture was left standing at room temperature in shading for 72 hours. The reaction mixture was purified by gel filtration with Sephacryl S-200 Superfine column (φ2.6×81 cm) manufactured by Pharmacia Corp., Sweden. The objective fraction was subjected to desalting and concentration by ultrafiltration with the use of YM-5 membrane manufactured by Amicon Corp., USA. The obtained solution containing the objective compound was further subjected to secondary purification by reversed phase high performance liquid chromatography with the use of YMC-ODS, A-211, 5 μ, φ4.6×250 mm column manufactured by Yamamura Chemicals to give the objective compound.

The results of the amino acid analysis by 24 hours' treatment for acid decomposition of the objective compound with 6N hydrochloric acid-phenol at 110° C. are as follows:

Asx. 3.09 (3); Glx. 2.26 (2); Ser. 2.86 (3);
Gly. 1.17 (1); Arg. 1.92 (3); Thr. 0.98 (1);
Ala. 2.95 (3); Tyr. 1.84 (2); Val. 1.03 (1);
Met. 1.10 (1); Ile. 1.84 (2); Leu.* 4.00 (4);
Phe. 1.01 (1); Lys. 2.03 (2)
* means standard amino acid and the figures in parentheses are theoretical values.

The behavior of the objective compound in high performance liquid chromatography is as follows:

Reversed phase high performance liquid chromatography

Column: YMC-ODS, A-211, 5 μ, φ4.6×250 mm (Manufactured by Yamamura Chemicals)
Eluent: Gradient
 A Solution: Water (0.1% trifluoroacetic acid)
 B Solution: Acetonitrile (0.1% trifluoroacetic acid)

Initial concentration of B Solution: 25%
Concentration gradient: 1%/min.
Flow rate: 1 ml/min.
Detection wavelength: 214 nm
Retention time: 21 9 minutes High performance gel filtration chromatography Column: TSK G3000PW $\phi$7.5×600 mm (Manufactured by TOSOH Corp.)
Eluent: 0.2M aqueous solution of sodium chloride
Flow rate: 0.6 ml/min.
Detection wavelength: 254 nm
Retention time: 23 minutes

EXAMPLE 8

Production of growth hormone-releasing factor [GRF(1-29)NH$_2$]III modified by a polyethylene glycol derivative (I)

To 10 mg of growth hormone-releasing factor [GRF(1-29)NH$_2$] in 5 ml of a 0.02M phosphoric acid buffer solution (pH 6.53) was added a solution of 43 mg of 4-monomethoxypolyethylene glycol-phenylglyoxal (1 equivalent amount relative to guanidino) and the mixture was left standing at room temperature in shading for 39 hours. The reaction mixture was purified by gel filtration with Sephacryl S-200 Superfine column ($\phi$2.6×81 cm) manufactured by Pharmacia, Corp., Sweden. The objective fraction was subjected to desalting and concentration by ultrafiltration with the use of YM-5 membrane manufactured by Amicon Corp., USA. The obtained solution containing the objective compound was further subjected to secondary purification by reversed phase high performance liquid chromatography with the use of YMC-ODS, A-211, 5 $\mu$, $\phi$4.6×250 mm column manufactured by Yamamura Chemicals to give the objective compound.

The results of the amino acid analysis by 24 hours' treatment for acid decomposition of the objective compound with 6N hydrochloric acid-phenol at 110° C. are as follows:

Asx. 2.63 (3); Glx. 2.00 (2); Ser. 2.65 (3);
Gly. 1.04 (1); Arg. 1.60 (3); Thr. 0.81 (1);
Ala. 2.96 (3); Tyr. 1.75 (2); Val. 1.01 (1);
Met. 1.19 (1); Ile. 1.83 (2); Leu.* 4.00 (4);
Phe. 0.85 (1); Lys. 1.95 (2)

* means standard amino acid and the figures in parentheses are theoretical values.

The behavior of the objective compound in high performance liquid chromatography is as follows:

Reversed phase high performance liquid chromatography

Column: YMC-ODS, A-211, 5 $\mu$, $\phi$4.6×250 mm (Manufactured by Yamamura Chemicals)
Eluent: Gradient
  A Solution: Water (0.1% trifluoroacetic acid)
  B Solution: Acetonitrile (0.1% trifluoroacetic acid)
  Initial concentration of B Solution: 25%
  Concentration gradient: 1%/min.
Flow rate: 1 ml/min.
Detection wavelength: 214 nm
Retention time: 21.9 minutes

EXAMPLE 9

Production of tissue-plasminogen activator (t-PA)III modified by a polyethylene glycol derivative (I)

To 170 $\mu$l of a tPA solution (5.0 mg/0.85% NaCl - 0.01% Tween 80) was added 5.0 ml of a 0.02M NaH$_2$PO$_4$ - H$_3$PO$_4$ solution containing 1M KSCN (pH 6.0) and the pH of the mixture was adjusted to 6.0 with 1N NaOH. To the mixture was added a solution of 66.5 mg of 4-monomethoxypolyethylene glycolphenylglyoxal (5 equivalent amount relative to guanidino) and the mixture was left standing at room temperature in shading for 16 hours. To the mixture was further added 66.5 mg of modification agent and the mixture was left standing in the same manner for 16 hours After eliminating excessive amount of modification agent and salts by ultrafiltration with the use of YM-30 membrane manufactured by Amicon Corp., USA, the mixture was subjected to gel filtration with Sephacryl S-200 column ($\phi$2.6×94 cm) manufactured by Pharmacia Corp., Sweden to give the fractions containing the objective compounds A and B. The obtained fractions were respectively subjected to desalting and concentration by ultrafiltration with the use of YM-30 membrane manufactured by Amicon Corp., USA, and thereby the aqueous solutions containing the objective compounds A and B were obtained.

The results of the amino acid analysis by 24 hours' treatment for acid decomposition of the objective compound A with 6N hydrochloric acid-phenol at 110° C. are as follows:

Asx. 47.5 (50); Glx. 54.8 (52); Ser. 45.4 (48);
Gly. 47.9 (43); His. 15.0 (16); Arg. 25.8 (35);
Thr. 20.7 (25); Ala. 31.8 (32); Pro. 29.4 (29);
Tyr. 22.3 (24); Val. 21.1 (25); Met. 4.30 (5);
Ile. 16.1 (19); Leu.* 39.0 (39); Phe. 17.1 (16);
Lys 22.8 (21)

* means standard amino acid and the figures in parentheses are theoretical values.

The behavior of the objective compound A in high performance liquid chromatography is as follows:

Reversed phase high performance liquid chromatography

Column: YMC-ODS, A-211, 5 $\mu$, $\phi$4.6×250 mm (Manufactured by Yamamura Chemicals)
Eluent: Gradient
  A Solution: Water (0.1% trifluoroacetic acid)
  B Solution: Acetonitrile (0.1% trifluoroacetic acid)
  Initial concentration of B Solution: 30%
  Concentration gradient : 1%/min.
Flow rate: 1 ml/min.
Detection wavelength: 214 nm
Retention time: 14.6 minutes High performance gel filtration chromatography Column: TSK G3000PW $\phi$7.5×600 mm (Manufactured by Toyo Soda Corp.)
Eluent: 0.2M aqueous solution of sodium chloride
Flow rate: 0.6 ml/min.
Detection wavelength: 254 nm
Retention time: 21.4 minutes The results of the amino acid analysis by 24 hours' treatment for acid decomposition of the objective compound B with 6N hydrochloric acid-phenol at 110° C. are as follows:

Asx. 46.5 (50); Glx. 48.0 (52); Ser. 46.3 (48);
Gly. 47.1 (43); His. 14.6 (16); Arg. 27.2 (35);
Thr. 21.2 (25); Ala. 32.1 (32); Pro. 30.4 (29);
Tyr. 24.2 (24); Val.. 21.9 (25); Met. 6.06 (5);
Ile. 16.5 (19); Leu.* 39.0 (39); Phe. 16.5 (16);
Lys. 20.9 (21)

* means standard amino acid and the figures in parentheses are theoretical values.

The behavior of the objective compound B in high performance liquid chromatography is as follows:

Reversed phase high performance liquid chromatography

Column: YMC-ODS, A-211, 5 μ, φ4.6×250 mm (Manufactured by Yamamura Chemicals)
Eluent: Gradient
  A Solution: Water (0.1% trifluoroacetic acid)
  B Solution: Acetonitrile (0.1% trifluoroacetic acid)
  Initial concentration of B Solution: 30%
  Concentration gradient: 1%/min.
Flow rate: 1 ml/min.
Detection wavelength: 214 nm
Retention time: 14.5 minutes High performance gel filtration chromatography Column TSK G3000PW φ7.5×600 mm (Manufactured by Toyo Soda Corp.)
Eluent: 0.2 M aqueous solution of sodium chloride
Flow rate: 0.6 ml/min.
Detection wavelength: 254 nm
Retention time: 22.1 minutes

EXAMPLE 10

Production of human Cu,Zn-superoxide dismutase (Cu,Zn-hSOD) modified by a polyethylene glycol derivative (I)

To 4.89 mg of human erythrocyte-derived Cu,Zn-hSOD manufactured by Sigma Corp. in 2.5 ml of a 0.2M $NaHCO_3$–0.02M $Na_2CO_3$ solution (pH 8.97) was added a solution of 70 mg of 4-monomethoxypolyethylene glycol-phenylglyoxal (10 equivalent amount relative to guanidino) and the mixture was stirred at room temperature in shading for 23.5 hours. After adjusting the pH of the reaction mixture to 5.0 with acetic acid, excessive amount of reagent and salts were eliminated therefrom by ultrafiltration with the use of YM-30 membrane manufactured by Amicon Corp., USA. The mixture was purified by gel filtration with Sephacryl S-200 column (φ2.6×94 cm) manufactured by Pharmacia Corp., Sweden. Thereafter, the mixture was subjected to desalting and concentration by ultrafiltration with the use of YM-30 membrane manufactured by Amicon Corp., USA, and thereby 10 ml of the solution containing the objective compound was obtained (contained protein: 14.0 μM).

The results of the amino acid analysis by 24 hours' treatment for acid decomposition of the objective compound with 6N hydrochloric acid-phenol at 110° C. are as follows:

Asx. 33.2 (36); Glx. 26.6 (26); Ser. 18.7 (20);
Gly. 49.4 (50); His. 14.1 (16); Arg. 4.7 (8);
Thr. 13.5 (16); Ala.* 20.0 (20); Pro. 11.1 (10);
Val. 26.2 (28); Ile. 13.1 (18); Leu. 19.6 (18);
Phe. 8.4 (8); Lys. 19.9 (22)

* means standard amino acid and the figures in parentheses are theoretical values.

By the above procedure, there was obtained SOD modified by a polyethylene glycol wherein the arginine residue is modified. The behavior of the objective compound in high performance liquid chromatography is as follows:

High performance gel filtration chromatography

Column: TSK G3000PW (φ7.5×600 mm) (Manufactured by Toyo Soda Corp.)
Eluent: 0.2M aqueous solution of sodium chloride
Flow rate: 0.6 ml/min.
Detection wavelength: 254 nm
Retention time: 20.6 minutes

EXAMPLE 11

Production of bovine Cu,Zn-superoxide dismutase modified by a polyethylene glycol derivative (I)

After 7.5 mg of bovine Cu,Zn-superoxide dismutase (Cu,Zn-bSOD) was dissolved in 1.875 ml of a 0.2M aqueous solution of $NaHCO_3$ (pH 8.5), a solution of 47.5 mg of 4-methoxypolyethylene glycol-phenylglyoxal obtained in Example 1 was added thereto and the mixture was reacted at room temperature in shading for 19 hours. After the termination of the reaction, 2 ml of water was added thereto and the pH thereof was adjusted to about 4 with 2N acetic acid. Thereafter, the mixture was purified by gel filtration with Sephacryl S-200 column [φ2,6×80 cm, eluent: a mixed solution of 0.1M acetic acid and 0.2 M sodium chloride (pH 2.8), flow rate: 2 ml/min.]. The fraction containing the objective compound was collected and subjected to desalting and concentration by ultrafiltration to give 10 ml of a 0.01M acetic acid solution containing the objective compound (contained protein: 4.2 mg).

The results of the amino acid analysis by 24 hours' treatment for acid decomposition of the objective compound with 6N hydrochloric acid at 110° C. are as follows:

Asx. 27.4 (34); Glx. 21.5 (22); Ser. 14.5 (16);
Gly. 42.1 (50); His. 12.7 (16); Arg. 5.7 (8);
Thr. 19.1 (24); Ala. 18.0* (18); Pro. 12.9 (12);
Tyr. 2.8 (2); Val. 22.4 (30); Met. 2.8 (2);
Ile. 12.8 (18); Leu. 17.1 (16); Phe. 8.4 (8);
Lys. 16.0 (20)

* means standard amino acid and the figures in parentheses are theoretical values.

The behavior of the objective compound in high performance liquid chromatography is as follows:

Reversed phase high performance liquid chromatography

Column: μ-Bondasphere-$C_{18}$ (φ3.9×150 mm) (Manufactured by Waters Corp.)
Eluent: Gradient
  A Solution: Water (0.1% trifluoroacetic acid)
  B Solution: Acetonitrile (0.1% trifluoroacetic acid)
  Initial concentration of B Solution: 35%
  Concentration gradient: 1%/min.
Flow rate: 1 ml/min.
Detection wavelength: 220 nm
Retention time: 12.3 minutes Molecular sieve high performance liquid chromatography Column : TSK G3000PW×L (φ7.8×300 mm)×2 (Manufactured by TOSOH Corp.)
Eluent: 0.2M aqueous solution of sodium chloride
Flow rate: 0.6 ml/min.
Detection wavelength: 254 nm
Retention time: 22.6 minutes

EXAMPLE 12

Production of insulin-like growth factor-1 (IGF-1) modified by a polyethylene glycol derivative (I)

To 4.3 mg of IGF-1 in 3.0 ml of a 0.2M $NaHCO_3$–0.02M $Na_2CO_3$ solution (pH 8.97) was added 20 μl of 2-methylmaleic anhydride 5 times at 10-minute intervals at room temperature under stirring, during which addition the pH of the reaction mixture was adjusted to 8-9 with 1N NaOH. The reaction mixture was further stirred at room temperature for 1 hour adjusting the pH thereof to 8-8.5 with 1N NaOH. Thereafter, 1 ml of the above buffer was added thereto and the pH thereof was adjusted to 8.97 with 1N NaOH. To the mixture was added a solution of 12.63 mg of 4-monomethoxypolyethylene glycolphenylglyoxal (0.7 equivalent amount relative to guanidino) obtained in Example 1 and the mixture was stirred at room temperature in shading for 16 hours. After adjusting the pH of the reaction mixture to 6.74 with acetic acid, the mixture was purified by gel filtration with Sephacryl S-200 column ($\phi$2.6×94 cm) manufactured by Pharmacia Corp., Sweden, and the objective fraction was subjected to desalting and concentration by ultrafiltration with the use of YM-10 membrane manufactured by Amicon Corp., USA. To the condensate was added acetic acid to thereby adjust the pH thereof to 2.12 and the mixture was stirred at 37° C. for 9.5 hours. Subsequent to neutralization with 1N NaOH, the mixture was subjected to desalting and concentration by ultrafiltration with the use of YM-10 membrane manufactured by Amicon Corp., USA, and further concentration by ultrafiltration with UFPI TGC manufactured by Millipore Corp., USA to give 500 $\mu$l of an aqueous solution containing the objective compound (contained protein: 148 $\mu$M).

The results of the amino acid analysis by 24 hours' treatment for acid decomposition of the objective compound with 6N hydrochloric acid-phenol at 110° C. are as follows:

Asx. 4.75 (5); Glx. 5.60 (6); Ser. 4.81 (5);
Gly. 6.96 (7); Arg. 3.58 (6); Thr. 2.95 (3);
Ala. 6.35 (6); Pro. 5.22 (5); Tyr. 3.08 (3);
Val. 2.37 (3); Met. 0.37 (1); Ile. 0.42 (1);
Leu.* 6.00 (6); Phe. 3.94 (4); Lys. 3.32 (3)

* means standard amino acid and the figures in parentheses are theoretical values.

From the above results, it is found that the Arg. residues are selectively modified. The behavior of the objective compound in high performance liquid chromatography is as follows:

Reversed phase high performance liquid chromatography

Column: YMC-ODS, A-211, 5 $\mu$, $\phi$4.6×250 mm (Manufactured by Yamamura Chemicals)
Eluent: Gradient
  A Solution: Water (0.1% trifluoroacetic acid)
  B Solution: Acetonitrile (0.1% trifluoroacetic acid)
  Initial concentration of B Solution: 25%
  Concentration gradient: 1%/min.
Flow rate: 1 ml/min.
Detection wavelength: 214 nm
Retention time: 21.0 minutes High performance gel filtration chromatography Column: TSK G3000PW $\phi$7.5×600 mm (Manufactured by Toyo Soda Corp.)
Eluent: 0.2M aqueous solution of sodium chloride
Flow rate: 0.6 ml/min.
Detection wavelength: 254 nm
Retention time: 21.6 minutes

EXAMPLE 13

Production of insulin-like growth factor-1(IGF-1)II modified by a polyethylene glycol derivative (I)

To 4.71 mg of IGF-1 in 2.0 ml of a 0.2M NaHCO$_3$-0.02M Na$_2$CO$_3$ solution (pH 8.97) was added 20 $\mu$l of 2-methylmaleic anhydride 5 times at 10-minute intervals at room temperature under stirring, during which addition the pH of the reaction mixture was adjusted to 8-9 with 1N NaOH. The reaction mixture was further stirred at room temperature for 1 hour adjusting the pH thereof to 8-8.5 with 1N NaOH. Thereafter, 1 ml of the above buffer was added thereto and the pH thereof was adjusted to 8.97 with 1N NaOH. To the mixture was added a solution of 3.3 mg of 4-monomethoxypolyethylene glycolphenylglyoxal (0.17 equivalent amount relative to guanidino) obtained in Example 1 and the mixture was stirred at room temperature in shading for 17 hours. The mixture was purified by gel filtration with Sephacryl S-200 column ($\phi$2.6×94 cm) manufactured by Pharmacia Corp., Sweden, and the objective fraction was subjected to desalting and concentration by ultrafiltration with the use of YM-10 membrane manufactured by Amicon Corp., USA. To the condensate was added acetic acid to thereby adjust the pH thereof to 2.12 and the mixture was stirred at 37° C. for 8 hours. Subsequent to neutralization with 1N NaOH, the mixture was subjected to desalting and concentration by ultrafiltration with the use of YM-10 membrane manufactured by Amicon Corp., USA, and further concentration by ultrafiltration with UFPI TGC manufactured by Millipore Corp., USA to give 500 $\mu$l of an aqueous solution containing the objective compound (contained protein: 133.5 $\mu$M).

The results of the amino acid analysis by 24 hours' treatment for acid decomposition of the objective compound with 6N hydrochloric acid-phenol at 110° C. are as follows:

Asx. 5.19 (5); Glx. 6.81 (6); Ser. 5.00 (5);
Gly. 7.21 (7); Arg. 4.14 (6); Thr. 3.01 (3);
Ala. 5.79 (6); Pro. 4.47 (5); Tyr. 2.68 (3);
Val. 2.65 (3); Met. 0.63 (1); Ile. 1.31 (1);
Leu.* 6.00 (6); Phe. 3.49 (4); Lys. 3.04 (3)

* means standard amino acid and the figures in parentheses are theoretical values.

By the above procedure, there was obtained IGF-1 modified to a lower degree by a polyethylene glycol. The behavior of the objective compound in high performance liquid chromatography is as follows:

Reversed phase high performance liquid chromatography

Column: YMC-ODS, A-211, 5 $\mu$, $\phi$4.6×250 mm (Manufactured by Yamamura Chemicals)
Eluent: Gradient
  A Solution: Water (0.1% trifluoroacetic acid)
  B Solution: Acetonitrile (0.1% trifluoroacetic acid)
  Initial concentration of B Solution: 25%
  Concentration gradient: 1%/min.
Flow rate: 1 ml/min.
Detection wavelength: 214 nm
Retention time: 19.2 minutes High performance gel filtration chromatography Column : TSK G3000PW $\phi$7.5×600 mm (Manufactured by Toyo Soda Corp.)
Eluent: 0.2M aqueous solution of sodium chloride
Flow rate: 0.6 ml/min.

Detection wavelength: 254 nm
Retention time: 23.1 minutes

EXAMPLE 14

Production of insulin-like growth factor (IGF-1)III modified by a polyethylene glycol derivative (I)

To 5.00 mg of IGF-1 in 2.0 ml of a 0.2M NaHCO$_3$–0.02M Na$_2$CO$_3$ solution (pH 8.97) was added 20 μl of 2-methylmaleic anhydride 5 times at 5-minute intervals at room temperature under stirring, during which addition the pH of the reaction mixture was adjusted to 8–9 with 1N NaOH. The reaction mixture was further stirred at room temperature for 1 hour adjusting the pH of the reaction mixture to 8–8.5 with 1N NaOH. Subsequent to the pH adjustment thereof to 8.97, 3.4 mg of 4-monomethoxypolyethylene glycol-phenylglyoxal (0.17 equivalent amount relative to guanidino) obtained in Example 1 was added thereto and the mixture was left standing at room temperature in shading for 16 hours. The reaction mixture was purified by gel filtration with Sephacryl S-200 column ($\phi$2.6×94 cm) manufactured by Pharmacia Corp., Sweden, and the objective fraction was subjected to desalting and concentration by ultrafiltration with the use of YM-10 membrane manufactured by Amicon Corp.; USA. To the condensate was added acetic acid to thereby adjust the pH thereof to 2.01 and the mixture was stirred at 40° C. for 11 hours. Subsequent to the pH adjustment thereof to 5.0 with 1N NaOH, the mixture was subjected to desalting and concentration by ultrafiltration with the use of YM-10 membrane manufactured by Amicon Corp., USA, and further concentration by ultrafiltration with UFPI TGC manufactured by Millipore Corp., USA, thereby obtaining 800 μl of an aqueous solution containing the objective compound (contained protein 144 μM).

The results of the amino acid analysis by 24 hours' treatment for acid decomposition of the objective compound with 6N hydrochloric acid-phenol at 110° C. are as follows:

Asx. 5.29 (5); Glx. 6.58 (6); Ser. 5.11 (5);
Gly. 8.47 (7); Arg. 4.67 (6); Thr. 2.76 (3);
Ala. 7.35 (6); Pro. 6.85 (5); Tyr. 3.08 (3);
Val. 2.63 (3); Met. 1.15 (1); Ile. 0.58 (1);
Leu.* 6.00 (6); Phe. 3.64 (4); Lys. 2.17 (3)

* means standard amino acid and the figures in parentheses are theoretical values.

The behavior of the objective compound in high performance liquid chromatography is as follows:

Reversed phase high performance liquid chromatography

Column: YMC-ODS, A-211, 5 μ, $\phi$4.6×250 mm (Manufactured by Yamamura Chemicals)
Eluent: Gradient
  A Solution: Water (0.1% trifluoroacetic acid)
  B Solution: Acetonitrile (0.1% trifluoroacetic acid)
  Initial concentration of B Solution: 25%
  Concentration gradient: 1%/min.
Flow rate: 1 ml/min.
Detection wavelength: 214 nm
Retention time: 17.4 minutes

High performance gel filtration chromatography

Column: TSK G3000PW $\phi$7.5×600 mm (Manufactured by Toyo Soda Corp.)
Eluent: 0.2M aqueous solution of sodium chloride
Flow rate: 0.6 ml/min.
Detection wavelength: 254 nm
Retention time: 24.7 minutes

EXAMPLE 15

Production of growth hormone-releasing factor [GRF(1-29)NH$_2$]IV modified by a polyethylene glycol derivative (I)

After 100 mg of growth hormone-releasing factor [GRF(1-29)NH$_2$] was dissolved in 50 ml of a 0.2M NaHCO$_3$- Na$_2$CO$_3$ solution (pH 9), 3 ml of an acetone solution containing 260 mg of maleic anhydride was added thereto under ice-cooling and the mixture was reacted under ice-cooling for 2 hours. After the termination of the reaction, the reaction mixture was subjected to preparative purification by high performance liquid chromatography with μ-Bondasphere-C$_{18}$ ($\phi$19×150 mm) column manufactured by Waters Corp. The elution of the objective compound was conducted with the concentration of acetonitrile enhanced from 30% to 75% at the rate of 1%/min. with the use of an aqueous solution of acetonitrile at the flow rate of 9.9 ml/min. The obtained fraction containing the objective compound was subjected to lyophilization to give 45 mg of maleyl-introduced GRF(1-29)NH$_2$. In a 0.2M NaHCO$_3$ solution (pH 8.2) was dissolved 15 mg of the thus-obtained maleyl-introduced GRF(1-29)NH$_2$, followed by addition of 615 mg of 4-methoxypolyethylene glycol-phenylglyoxal obtained in Example 1, and the mixture was reacted at room temperature in the dark for 8 hours. After the termination of the reaction, the mixture was neutralized with 1N acetic acid and subjected to gel filtration with Sephacryl S-200 column ($\phi$2.6×94 cm, eluent: 0.2M aqueous solution of sodium chloride, flow rate: 2 ml/min.) in two times of conduct. The fraction containing the objective compound was collected, desalted and concentrated to give 4.5 ml of the solution containing the objective compound. Subsequently, 2.5 ml of an aqueous solution of 2N acetic acid was added to 2.5 ml of this solution and the mixture was reacted at 37° C. for 40 hours. After demaleylation, there could be obtained the objective growth hormone-releasing factor [GRF(1-29)NH$_2$] modified by a polyethylene glycol derivative (I).

The results of the amino acid analysis by 24 hours' treatment for acid decomposition of the objective compound with 6N hydrochloric acid at 110° C. are as follows:

Asx. 3.06 (3); Glx. 1.97 (2); Ser. 2.80 (3);
Gly. 1.02 (1); Arg. 1.19 (3); Thr. 1.03 (1);
Ala. 3.32 (3); Tyr. 1.99 (2); Val. 1.04 (1);
Met. 1.09 (1); Ile. 2.09 (2); Leu* 4.00 (4);
Phe. 1.09 (1); Lys. 1.84 (2)

* means standard amino acid and the figures in parentheses are theoretical values.

The behavior of the objective compound in high performance liquid chromatography is as follows:

Reversed phase high performance liquid chromatography

Column: μ-Bondasphere-C$_{18}$ ($\phi$3.9×150 mm) (Manufactured by Waters Corp.)
Eluent: Gradient
  A Solution: Water (0.1% trifluoroacetic acid)
  B Solution: Acetonitrile (0.1% trifluoroacetic acid)
  Initial concentration of B Solution: 35%
  Concentration gradient: 2%/min.
Flow rate: 1 ml/min.
Detection wavelength: 220 nm Retention time: 10.5 minutes Molecular sieve high performance liquid chromatography Column: TSK G3000PW $\phi$7.5×600 mm (Manufactured by TOSOH Corp.)
Eluent: 0.2M aqueous solution of sodium chloride
Flow rate: 0.6 ml/min.
Detection wavelength: 254 nm
Retention time: 22.1 minutes

EXAMPLE 16

Production of human Cu,Zn-superoxide dismutase (Cu,Zn-hSOD) II modified by a polyethylene glycol derivative (I)

To 15.12 mg of human erythrocyte-derived Cu,Zn-hSOD manufactured by Sigma Corp. in 7.5 ml of a 0.2M NaHCO$_3$–0.02M Na$_2$CO$_3$ solution (pH 9.25) was added a solution of 19.6 mg of 4-monomethoxypolyethylene glycol-phenylglyoxal (1 equivalent amount relative to guanidino) and the mixture was stirred at room temperature in shading for 8 hours. And then 39.2 mg of 4-monomethoxypolyethylene glycol phenylglyoxal (2 equivalent amount relative to guanidino) was added to the solution and the mixture was stirred at room temperature in shading for 16 hours. After adjusting the pH of the reaction mixture to 6.95 with 2N-acetic acid, the mixture was purified by gel filtration with Sephacryl S-200 column ($\phi$2.6×94 cm) manufactured by Pharmacia Corp., Sweden, and high performance gel filtration (TSK G3000SW) to give a fraction containing the objective compound A and a fraction containing the objective compound B. Thereafter, each fraction was subjected to desalting and concentration by ultrafiltration with the use of YM-30 membrane manufactured by Amicon Corp., USA, and thereby 1.8 ml of the solution containing the objective compound A and 1.8 ml of the solution containing the objective compound B were obtained (contained protein : A 1.78 mg/ml, B 460 μg/ml).

The results of the amino acid analysis by 24 hours' treatment for acid decomposition of the objective compound A with 6N hydrochloric acid-phenol at 110° C. are as follows:

Asx. 33.5 (36); Glx. 26.0 (26); Ser. 18.7 (20);
Gly. 49.0 (50); His. 16.8 (16); Arg. 6.21 (8);
Thr. 14.7 (16); Ala.* 20.0 (20); Pro. 10.9 (10);
Val. 25.8 (28); Ile. 13.9 (18); Leu. 19.4 (18);
Phe. 8.1 (8); Lys. 18.3 (22)
* means standard amino acid and the figures in the parentheses are theoretical values.

The behavior of the objective compound A in high performance liquid chromatography is as follows:

High performance gel filtration chromatography

Column: TSK G3000SW ($\phi$7.5×600 mm) (Manufactured by Toyo Soda Corp.)
Eluent: 0.2M aqueous solution of sodium chloride (contain 5% EtOH)
Flow rate: 0.6 ml/min.
Detection wavelength: 220 nm
Retention time: 22.45 minutes The results of the amino acid analysis by 24 hours' treatment for acid decomposition of the objective compound B with 6N hydrochloric acid-phenol at 110° C. are as follows:

Asx. 34.2 (36); Glx. 26.5 (26); Ser. 18.4 (20);
Gly. 48.8 (50); His. 16.4 (16); Arg. 7.03 (8);
Thr. 14.6 (16); Ala.* 20.0 (20); Pro. 11.0 (10);
Val. 25.4 (28); Ile. 13.1 (18); Leu. 18.4 (18);
Phe. 7.4 (8); Lys. 17.1 (22)
* means standard amino acid and the figures in parentheses are theoretical values.

The behavior of the objective compound B in high performance liquid chromatography is as follows:

High performance gel filtration chromatography

Column: TSK G3000SW ($\phi$7.5×600 mm) (Manufactured by Toyo Soda Corp.)
Eluent: 0.2M aqueous solution of sodium chloride (contain 5% EtOH)
Flow rate: 0.6 ml/min.
Detection wavelength: 220 nm
Retention time: 25.16 minutes

EXAMPLE 17

Production of human Cu,Zn-superoxide dismutase (Cu,Zn-hSOD) III modified by a polyethylene glycol derivative (I)

To 10.20 mg of human erythrocyte-derived Cu,Zn-hSOD manufactured by Sigma Corp. in 5.0 ml of a 0.2M NaHCO$_3$–0.02M Na$_2$CO$_3$ solution (pH 9.25) was added a solution of 70 mg of 4-monomethoxypolyethylene glycol-phenylglyoxal (5 equivalent amount relative to guanidino) and the mixture was stirred at room temperature in shading for 18 hours. After adjusting the pH of the reaction mixture to 6.9 with 2N-acetic acid, the mixture was purified by gel filtration with Sephacryl S-200 column ($\phi$2.6×94 cm) manufactured by Pharmacia Corp., Sweden. Thereafter, a fraction containing the objective compound was subjected to desalting and concentration by ultrafiltration with the use of YM-30 membrane manufactured by Amicon Corp., USA, and thereby 1.8 ml of the solution containing the objective compound was obtained (contained protein: 1.59 mg/ml).

The results of the amino acid analysis by 24 hours' treatment for acid decomposition of the objective compound with 6N hydrochloric acid-phenol at 110° C. are as follows:

Asx. 33.0 (36); Glx. 26.2 (26); Ser. 18.6 (20);
Gly. 48.2 (50); His. 16.4 (16); Arg. 5.89 (8);
Thr. 14.4 (16); Ala.* 20.0 (20); Pro. 11.1 (10);
Val. 26.4 (28); Ile. 13.9 (18); Leu. 19.5 (18);
Phe. 7.9 (8); Lys. 17.0 (22)
* means standard amino acid and the figures in the parentheses are theoretical values.

By the above procedure, there was obtained SOD modified by a polyethylene glycol wherein the arginine residue is modified. The behavior of the objective compound in high performance liquid chromatography is as follows:

High performance gel filtration chromatography

Column: TSK G3000SW ($\phi$7.5×600 mm) (Manufactured by Toyo Soda Corp.)
Eluent: 0.2M aqueous solution of sodium chloride (contain 5% EtOH)
Flow rate: 0.6 ml/min.
Detection wavelength: 220 nm
Retention time: 20.79 minutes

EXAMPLE 18

Production of human Cu,Zn-superoxide dismutase (Cu,Zn-hSOD) IV modified by a polyethylene glycol derivative (I)

To 4.92 mg of human erythrocyte-derived Cu,Zn-hSOD manufactured by Sigma Corp. in 2.5 ml of a 0.2 M $NaHCO_3$–0.02M $Na_2CO_3$ solution (pH 9.25) was added a solution of 70 mg of 4-monomethoxypolyethylene glycol-phenylglyoxal (10 equivalent amount relative to guanidino) and the mixture was stirred at room temperature in shading for 24 hours. After adjusting the pH of the reaction mixture to 6.89 with 2N-acetic acid, the mixture was purified by gel filtration with Sephacryl S-200 column ($\phi$2.6×94 cm) manufactured by Pharmacia Corp., Sweden. Thereafter, a fraction containing the objective compound was subjected to desalting and concentration by ultrafiltration with the use of YM-30 membrane manufactured by Amicon Corp., USA, and thereby 1.8 ml of the solution containing the objective compound was obtained (contained protein: 1.34 mg/ml).

The results of the amino acid analysis by 24 hours' treatment for acid decomposition of the objective compound with 6N hydrochloric acid-phenol at 110° C. are as follows:

Asx. 33.1 (36); Glx. 24.9 (26); Ser. 18.6 (20);
Gly. 48.7 (50); His. 16.8 (16); Arg. 5.5 (8);
Thr. 14.5 (16); Ala.* 20.0 (20); Pro. 11.4 (10);
Val. 25.1 (28); Ile. 13.2 (18); Leu. 18.5 (18);
Phe. 7.3 (8); Lys. 15.0 (22)

* means standard amino acid and the figures in parentheses are theoretical values.

By the above procedure, there was obtained SOD modified by a polyethylene glycol wherein the arginine residue is modified. The behavior of the objective compound in high performance liquid chromatography is as follows:

High performance gel filtration chromatography

Column: TSK G3000SW ($\phi$7.5×600 mm) (Manufactured by Toyo Soda Corp.)
Eluent: 0.2M aqueous solution of sodium chloride (Contain 5% EtOH)
Flow rate: 0.6 ml/min.
Detection wavelength: 220 nm
Retention time: 19.58 minutes

What is claimed is:

1. A polyethylene glycol derivative of the formula

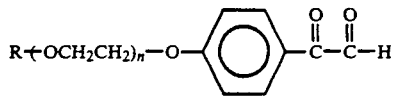

wherein R represents a lower alkyl and n represents a positive integer which renders the average molecular weight of the polyethylene glycol moiety about 1,000–12,000.

2. The polyethylene glycol derivative as claimed in claim 1 which is 4-monomethoxypolyethylene glycol-phenylglyoxal.

* * * * *